United States Patent
Alt et al.

(10) Patent No.: US 6,238,340 B1
(45) Date of Patent: May 29, 2001

(54) COMPOSITE MATERIALS FOR AVOIDANCE OF UNWANTED RADIATION AMPLIFICATION

(76) Inventors: Eckhard Alt, Eichendorffstrasse 52, 85521 Ottobrunn (DE); D. F. Regulla, Behamstrasse 17, 80687 Munich (DE)

( * ) Notice: Subject to any disclaimer, the term of this patent is extended or adjusted under 35 U.S.C. 154(b) by 0 days.

(21) Appl. No.: 09/081,953

(22) Filed: May 19, 1998

(51) Int. Cl.$^7$ ........................................ A61B 6/00
(52) U.S. Cl. ........................ 600/431; 600/433; 600/373
(58) Field of Search ........................ 600/431, 433, 600/434, 435, 424, 420, 373; 604/271, 280; 424/426

(56) References Cited

U.S. PATENT DOCUMENTS

| | | | |
|---|---|---|---|
| 3,302,635 | * | 2/1967 | Pittman . |
| 3,659,588 | * | 5/1972 | Kahn et al. . |
| 4,990,138 | * | 2/1991 | Bacich et al. .................. 604/96 |
| 5,143,089 | * | 9/1992 | Alt ................................. 128/784 |
| 5,171,232 | * | 12/1992 | Castillo et al. ................ 604/280 |
| 5,360,666 | * | 11/1994 | Eichmiller . |
| 5,437,290 | * | 8/1995 | Bolger et al. . |
| 5,626,136 | * | 5/1997 | Webster, Jr. . |
| 5,679,470 | * | 10/1997 | Mayer . |
| 5,682,894 | * | 11/1997 | Orr et al. ........................ 128/654 |
| 5,782,764 | * | 7/1998 | Werne ............................ 600/411 |
| 5,788,979 | * | 8/1998 | Alt et al. ........................ 424/426 |
| 5,817,017 | * | 10/1998 | Young et al. .................. 600/433 |
| 5,824,026 | * | 10/1998 | Diaz . |
| 5,843,148 | * | 12/1998 | Gijsbers et al. . |

* cited by examiner

*Primary Examiner*—Marvin M. Lateef
*Assistant Examiner*—Shawna J Shaw

(57) ABSTRACT

An unwanted effect of secondary radiation enhancement from backscatter of incident ionizing radiation on a relatively extensive metallic portion of an instrument to be inserted into a human body under x-ray fluoroscopy is minimized by coating the metallic surface thereof with a biocompatible material having the characteristic of shielding the secondary radiation enhancement effect from reaching body tissue. The depth of penetration of the secondary radiation enhancement is dependent on the atomic number of the metallic portion in conjunction with the expected radiation characteristics and energy level of the radiation incident on the metallic surface. The coating material is selected according to the atomic number of the metallic portion, and the coating has a thickness at least equal to the anticipated depth of penetration of the secondary radiation enhancement, as the shielding characteristic of the coating material, so that the secondary radiation enhancement effect will dissipate before reaching the body tissue.

21 Claims, 1 Drawing Sheet

COMPOSITE MATERIALS FOR AVOIDANCE OF UNWANTED RADIATION AMPLIFICATION

BACKGROUND OF THE INVENTION

The present invention relates to methods and devices for providing considerable fluoroscopic visibility and high electrical conductivity without the undesired effects of secondary local dose enhancement of x-ray radiation.

In co-pending U.S. patent application Ser. No. 09/081,954 ("the '954 application") the applicants herein disclose methods and systems for providing differential local dose enhancement of incident ionizing radiation for purposes of inhibiting tissue cell proliferation, which may include suppression of neointimal hyperplasia that characterizes restenosis such as that following coronary or carotid artery angioplasty or trauma to other body vessels, ducts or tracts, or destruction of malignant tumors.

An x-ray source can generate a beam of radiation with an energy content in a range from 10 KeV (000's of electron Volts) to 400 MeV. If a radiation beam of several hundred KeV contacts a metal surface, it was assumed in the past that the dosage of x-ray radiation is amplified by a factor of from 1.8 to 2.5 at the metal surface owing to backscatter radiation, which is attributable to a photo-multiplier effect. Amplification by such a factor had not been deemed either useful or dangerous. The applicants herein discovered in their research, however, that at radiation energy levels below about 400 KeV the amplification factor from backscatter from the metallic surface is inversely proportional to the KeV level of the radiation and, in the vicinity of the metal structures, can be 100 times the radiation dosage that exists in the same location in the absence of such structures. An increasingly higher amplification factor is experienced at the metal surface for increasingly lower radiation intensity, with a maximum factor of about 200× occurring for a radiation level of 40 KeV. The applicants further found that the range and intensity of the backscatter radiation depends on the physical characteristics of the metal surface, particularly on the atomic number of the metal, expressed as Z, in the periodic table of elements. A maximum backscatter radiation effect occurs at Z=60, corresponding to the atomic number for the element iodine, and a reduction in backscatter amplification occurs for metals with atomic numbers lower or higher than 60. The noble metals such as gold, platinum and iridium, for example, are at about Z=80, which yields an amplification factor of about 100.

As disclosed in the co-pending '954 application, the amplification effect enables a closely controlled local dosage enhancement of impinging radiation for therapeutic applications involving tissue cell proliferation found in vascular restenosis and solid tumors. A radiation dosage of 20 Gray (Gy) is effective to inhibit proliferation of smooth muscle cells in a carotid artery following angioplasty. However, by implanting (or employing a previous implant of) a metallic stent which is used to hold open the lumen of the artery at the angioplasty site, and irradiating the adjacent tissue with the stent in place, the amplification from backscatter radiation can enhance the dosage to the tissue of interest to allow use of radiation of lower intensity. Moreover, if the stent has a coating of a noble metal, a beam of x-ray radiation of about 40 KeV incident on that metal surface can deliver a dosage at that location of approximately 100× the dosage that would be delivered without the presence of the metal surface despite even use of a beam of considerably higher level of energy content. Thus, a system and method which would produce a dosage of only 0.20 Gy to tissue at a site of interest can be made to yield an effective dosage of 20 Gy by use of the principles of that invention.

Despite these advantages which are attainable by beneficial use of this secondary local dose enhancement, and the improvements thereof provided by the invention of the co-pending application, there remain situations in which such secondary enhancement attributable to the presence of a metallic surface in an environment in which a region of the body is being irradiated with ionizing radiation is highly undesirable.

It is a principal aim of the present invention to provide methods and means of avoiding unwanted amplification of incident radiation where metal surfaces are present.

Various routine investigations or examinations of a patient for diagnostic purposes, such as in the field of electrophysiology, require the use of a number of catheters which are inserted into the patient's body. By way of example, ablation procedures call for the placement of mapping catheters in firm contact with the heart so as to evoke responses of the heart to signals transmitted from an external electrical physiological work station, and to detect intrinsic electrical signals of cardiac activity which are recorded at the work station. Metallic surfaces of electrodes on the catheters serve not only to enable transmission and reception of these signals, but to enhance the visibility of the catheters under x-ray fluoroscopy for precise placement. The higher the atomic number of the metal used for the electrodes, the more enhanced is the fluoroscopic visibility. Accordingly, the noble metals are typically used, if only as a surface coating, for this purpose.

As pointed out above with reference to co-pending '954 application, however, even relatively low level x-ray radiation used for fluoroscopy can be significantly multiplied to deliver harmful dosages of ionizing radiation to body tissue in the immediate vicinity of the metallic surfaces. In research performed by one of the applicants herein, measurement of the physical and biological interface dose effects in tissue attributable to x-ray released secondary radiation from metallic gold surfaces indicates that the number of oncogenic transformations (i.e., gene-induced transformation of cells from normal proliferation to a potentially malignant state) increases by a factor of 20 at dose levels generally considered to be safe—about 100 micro-Gray (mGy). This increase in transformed oncogenic cells depends on the presence of metallic surfaces and their effect in amplifying radiation dosage, and is clearly undesirable.

Accordingly, a more specific objective of the invention is to provide a metallic catheter or other medical investigative device to be placed in the body for examining, exploratory, diagnostic or related purposes—even therapeutic, where the amplification effect of radiation dosage disclosed in the above co-pending application is not sought—, and in which the metallic surface renders the device adequately visible under fluoroscopy, but which is implemented with safeguards to avoid the oncogenic effect attributable to incidence of x-ray radiation on the metallic surface.

SUMMARY OF THE INVENTION

According to a preferred embodiment of the invention, the metallic surface of the device to be inserted or implanted into the patient's body is retained, but a coating is applied to the surface of sufficient thickness or other predetermined characteristics to absorb or shield the extent of penetration of the secondary or differential local enhancement of radiation dosage. It is known from the aforementioned co-pending '954 application that the backscatter radiation that results from ionizing radiation incident on the metal surface—while it may be intense depending upon the level of the incident radiation and the atomic number of the metallic surface—has a relatively short range or depth of penetration. For example, for a typical diagnostic radiation process, energies in a range from 60 KeV to 120 KeV are applied to the patient. This energy range is also typical of fluoroscopic techniques using x-ray radiation, in which the physician is viewing the path or location of a catheter or other implantable device during a surgical or medical procedure. In such instances, where the beam of radiation is impinging on a surface of noble metal such as gold or platinum, the range of penetration of the backscatter radiation is up to approximately 100 micrometers or microns ($\mu$m).

By adding a shielding or absorbing layer or coating of suitable material atop the metal surface, the metal allows the device on which it is used, when implanted or inserted into the body, to be observed by x-ray fluoroscopy. But if the shielding layer is sufficiently thick, e.g., from 50 to 150 $\mu$m (at least 100 $\mu$m in the example mentioned above), it prevents the backscatter radiation from reaching healthy tissue. The thickness of the coating material can be determined in practice from the estimated or anticipated energy level of the incident radiation, and the atomic number of the metal. It is imperative that the shielding material be biologically compatible (i.e., biocompatible) with the fluids and tissue of the body. Examples of suitable material for this purpose include polyurethane or polyethylene.

It is therefore another important aim of the present invention to provide a method and means for protecting the patient against local dose enhancement of ionizing radiation incident on a metal surface of a diagnostic, exploratory or therapeutic tool, by coating the metal surface with an inert material of sufficient thickness to prevent penetration of backscatter radiation into fluids or tissue of the body.

According to another embodiment of the invention, the unwanted effect of secondary radiation enhancement that derives from the presence of a metal surface on which the beam of radiation impinges, is recognized as being attributable in large part to the metal having a high atomic number, which also contributes to its good visibility by virtue of the radiopacity of such metals. Lowering the atomic number, by appropriate selection of the metal, would reduce the unwanted effect of secondary radiation enhancement from backscatter, but would also lower the fluoroscopic visibility. If, however, a material is selected which is close to the atomic number of the body tissue, i.e., Z=7.2, then the secondary radiation enhancement is minimized because no differential effect exists between that material and normal human tissue and blood.

In particular, according to this embodiment, a carbon coating is applied to the metal surface to take advantage of carbon's atomic number (Z=6) which is very close to that of body tissue. Additionally, as disclosed in U.S. Pat. No. 5,143,089, issued Sep. 1, 1992, and as well in German patent DE 3607302C2, of one of the applicants herein, carbon preparations can be made electrically conductive as with isotropic carbon fibers described therein. In this way, the coating can provide the desired secondary radiation shielding or absorption capability, while also offering desirable electrical conductivity as an electrode for communicating electrical signals to and from the by tissue or organs with which the electrode is in contact or in close proximity. Thus, in the case of ablation procedures requiring mapping catheters in firm contact with the heart for stimulating with, and detecting, electrical signals for communication from and to an external work station, for example, coating the electrode with an electrically conductive carbon preparation would minimize the local enhancement of differential or secondary radiation effect when the mapping catheters are being positioned or otherwise viewed by fluoroscope, while yielding excellent conductivity.

Hence, yet another aim of the invention is to provide a catheter having the characteristics of excellent fluoroscopic visibility together with excellent electrical conductivity, and which also avoids the unwanted effect of secondary local dose enhancement of x-ray radiation to which it is subjected during fluoroscopy.

BRIEF DESCRIPTION OF THE DRAWINGS

The above and other aims, aspects, features and attendant advantages of the invention will be further understood from the following detailed description of the best mode presently contemplated for practicing the invention, by reference to presently preferred embodiments and methods, taken in conjunction with the accompanying drawings, in which.

DETAILED DESCRIPTION OF THE PREFERRED EMBODIMENTS AND METHODS

Figure 1:
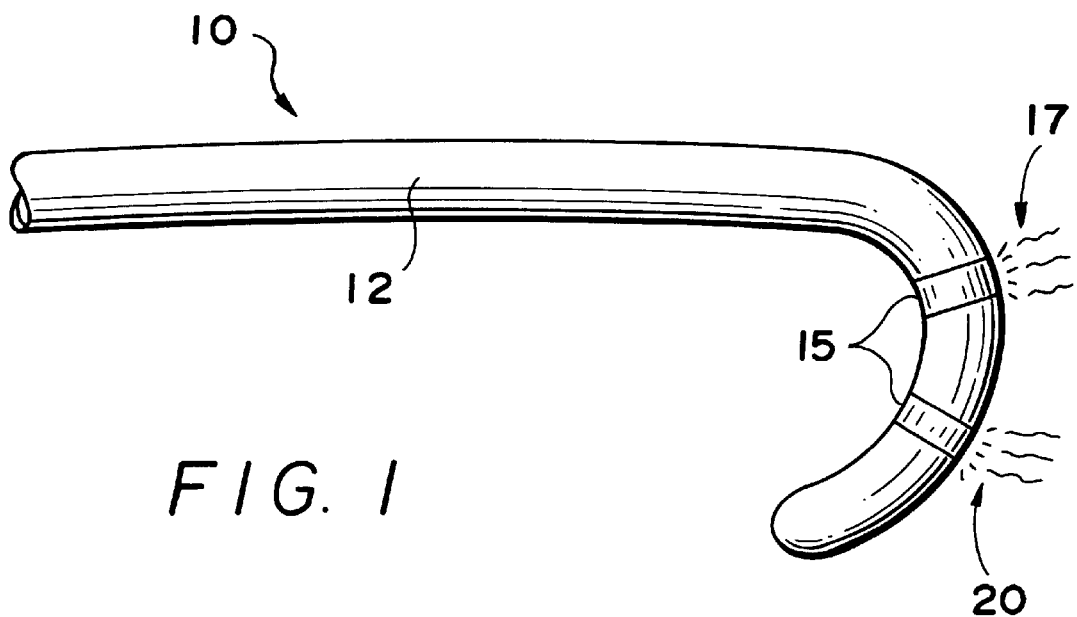
FIG. 1 is a perspective view of a catheter employing the principles and fabricated by the method of the invention.

Referring to FIG. 1, a catheter 10 which is to be inserted, implanted and/or positioned in the body of a human patient with the aid of x-ray fluoroscopy includes an elongate catheter body 12, which is generally composed of an electrically non-conductive or insulative material conventionally employed for medical purposes, and specifically for biocompatibility with the tissue and blood of the body. The Figure is not intended to be to scale. In the particular example of FIG. 1, the catheter has one or more exposed metallic surfaces consisting of metal bands 15. Each band may, for example, constitute an electrode which is electrically connected to a conductive lead (not shown) that runs through a lumen in catheter body 12 to an electrical connector (not shown) which is to be positioned external to the body for electrical connection to an electrophysiology work station (not shown). In practice, such a catheter might be used for performing a diagnostic, investigative, exploratory or therapeutic function when inserted into the body of the patient. In any of those functions, the metal band or bands make electrical contact with the tissue or fluids of the body, so that predetermined electrical signals from the work station may be delivered to the tissue for purposes of electrical stimulation thereof, and/or intrinsic electrical signals arising from activity of the body, such as cardiac activity, may be detected and transmitted to the work station. It will be understood that this is merely an example of a possible function, and the catheter or any other body implantable instrument may be used for a different purpose entirely.

In any event, as a consequence of the use of x-ray fluoroscopy to enable physician viewing of the metal surface(s) of band(s) 15, which by virtue of its metal composition, is visible as a shadow on the fluoroscope, ionizing radiation from the x-rays (depicted by wavy lines 17 in FIG. 1) is incident or impinges on the metallic surface(s) 15. The effect of this is to produce secondary radiation enhancement from backscatter (depicted by reflected wavy lines 20 in the Figure) of the incident radiation from the metallic surface.

The incident radiation of the x-rays will have an energy level which is typically in a range of 40 KeV to 120 KeV that tends to promote this secondary radiation enhancement. Thus, while the incident radiation itself is of relatively low level, this secondary enhancement effect can deliver a radiation dosage to body tissue or blood cells in contact with or in close proximity to the metal surface 15 of the catheter body 12 which is sufficiently high to have a harmful and even lethal effect on the tissue or the blood, especially on the white blood cells such as lymphocytes, granulocytes and monocytes. While the depth of penetration of this secondary radiation is relatively shallow, ranging up to 150 $\mu$m from the metallic surface, for example, its harmful effect is pronounced.

This secondary radiation enhancement effect is even more pronounced with metals having relatively high atomic numbers, in a range from Z=40 to Z=80 found in many of the noble metals, for example. This is precisely the more desirable range of atomic numbers for high visibility of the metal surface on the fluoroscope. Clearly, this secondary radiation enhancement is an unwanted effect to be avoided or at least minimized where ordinary diagnostic, exploratory, investigative or therapeutic functions of the instrument are being utilized in the procedure.

Figure 2:
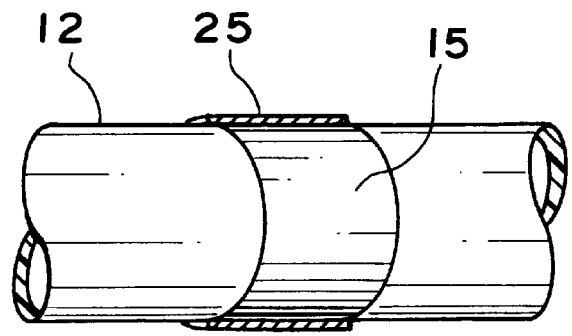
FIG. 2 is a detailed view of a coating on a metallic surface of the catheter.

According to the invention, to that end, after the instrument such as catheter 10 to be inserted into the body is fabricated, the metallic surface 15 thereof is coated with a biocompatible material 25 (FIG. 2) witch has been selected or applied to have a characteristic of shielding the secondary radiation enhancement effect from reaching body tissue. In general, the coating material will be selected according to the atomic number of the metallic surface, which, together with the energy level of the incident ionizing radiation, determines the depth of penetration of the secondary radiation. Of course, this coating is applied or formed atop the metallic surface before making the instrument available for insertion into the body.

Preferably, in the coating step the coating material 25 is built up to a thickness overlying the metallic surface which is at least equal to the anticipated depth of penetration of the secondary radiation enhancement, as the shielding characteristic, so that the secondary radiation enhancement effect will dissipate before reaching the body tissue. The depth of penetration of the secondary radiation enhancement is determined by reference to the atomic number of the metallic surface in conjunction with the expected energy level of the radiation incident on the metallic surface. In one embodiment of the invention, the preferred coating material is polyurethane and polyethylene, and the coating 25 is built up to a thickness in a range from about 50 $\mu$m to about 150 $\mu$m.

In another embodiment of the invention, the coating material 25 is selected according to have an atomic number which is considerably closer to the atomic number of body tissue (Z=7.2) than is the atomic number of the metallic surface. By so doing, the differential effect between the surface of incidence and the body tissue, which produces the secondary radiation enhancement that results from backscatter from the metallic surface, is significantly reduced. To avoid a loss of electrical conductivity in those instances where the metallic surface serves as an electrode or otherwise is used for that property, an electrically conductive material is selected for the coating 25. Preferably, the selected material is a preparation of carbon, such as described in U.S. Pat. No. 5,143,089 or in German patent DE 3607302C2, each of which was issued to one of the applicants herein. The pertinent portion of the disclosures of those patents is incorporated herein by reference. As pointed out therein, the selected preparation of carbon can be, and preferably is, made electrically conductive and isotropic. In this embodiment, the carbon coating is built up to a thickness which is preferably in a range from about 50 $\mu$m to about 150 $\mu$m, and most preferably to a thickness not exceeding about 100 $\mu$m, particularly where the underlying metallic surface is a noble metal.

Although certain preferred embodiments and methods have been disclosed herein, it will be appreciated by those skilled in the art to which the invention pertains, from a consideration of the foregoing description, that variations and modifications may be made with respect to these examples without departing from the spirit and scope of the invention. Accordingly, it is intended that the invention shall be limited only by the appended claims and the rules and principles of applicable law.

What is claimed is:

1. A method of avoiding an unwanted effect of secondary radiation enhancement from backscatter of incident ionizing radiation on a metallic surface of an instrument to be inserted into a human body under x-ray fluoroscopy, which comprises the steps of designating an instrument having said metallic surface thereon for insertion into a body, and, before making said designated instrument available for said insertion, coating said metallic surface thereof with a biocompatible material having a characteristic of shielding the secondary radiation enhancement effect from reaching body tissue or blood, including selecting said coating material according to the atomic number of said metallic surface.

2. The method of claim 1, including in said coating step, applying said coating material to a thickness at least substantially equal to the anticipated depth of penetration of the secondary radiation enhancement, so that the secondary radiation enhancement effect will dissipate before reaching body tissue.

3. The method of claim 2, including in the step of selecting said coating material according to the atomic number of said metallic surface, determining an estimated depth of penetration of the secondary radiation enhancement from said atomic number of the metallic surface in conjunction with the expected energy level of the radiation incident on said metallic surface.

4. The method of claim 3, wherein the coating material is selected from a group consisting of polyurethane and polyethylene.

5. The method of claim 3, including in said coating step, applying said coating material to a thickness in a range from about 50 $\mu$m to about 150 $\mu$m.

6. The method of claim 1, including in the step of selecting said coating material according to the atomic number of said metallic surface, selecting a suitable coating material with an atomic number which is considerably closer to the atomic number of body tissue than the atomic number of said metallic surface, to reduce a differential effect and, thereby, the secondary radiation enhancement resulting from backscatter.

7. The method of claim 6, including selecting an electrically conductive material as the coating material.

8. The method of claim 6, including selecting a preparation of carbon as the coating material.

9. The method of claim 8, wherein the selected preparation of carbon is electrically conductive.

10. The method of claim 8, including in said coating step, applying said selected preparation of carbon to a thickness in a range from about 50 $\mu$m to about 150 $\mu$m.

11. The method of claim 10, including applying said selected preparation of carbon to a thickness not exceeding about 100 $\mu$m.

12. A device adapted to be inserted into a human body for performing a diagnostic, exploratory or therapeutic function, comprising at least a partial continuous metallic surface extending over a substantial portion of and in direct contact with the body of said device to render said portion of said device highly visible for proper positioning thereof in the human body under x-ray fluoroscopy, and a coating of a biocompatible material on said metallic surface having a characteristic of shielding the effect of secondary radiation enhancement arising from backscatter of x-ray radiation incident on said metallic surface from reaching human body tissue, wherein said biocompatible material for the coating is electrically conductive and has an atomic number which is considerably closer to the atomic number of body tissue than the atomic number of the metallic surface.

13. A device adapted to be inserted into a human body for performing a diagnostic, exploratory or therapeutic function, comprising at least a partial continuous metallic surface extending over a substantial portion of and in direct contact with the body of said device to render said portion of said device highly visible for proper positioning thereof in the human body under x-ray fluoroscopy, and a coating of a biocompatible material on said metallic surface having a characteristic of shielding the effect of secondary radiation enhancement arising from backscatter of x-ray radiation incident on said metallic surface from reaching human body tissue, wherein said biocompatible material for the coating is a carbon preparation with an atomic number which is considerably closer to the atomic number of body tissue than the atomic number of the metallic surface.

14. The device of claim 13, wherein said carbon preparation is electrically conductive.

15. The device of claim 13, wherein said carbon preparation coating has a thickness in a range from about 50 $\mu$m to about 150 $\mu$m.

16. The device of claim 15, wherein said carbon preparation coating has a thickness not exceeding about 100 $\mu$m.

17. A catheter adapted to be positioned in the body of a patient for performing a diagnostic, exploratory or therapeutic function, said catheter comprising an elongate body, the catheter body being predominantly non-metallic and having at least a continuous exposed metallic surface extending over a substantial portion of and in direct contact with a non-metallic part of the catheter body to render said portion of the catheter highly visible during positioning thereof in the patient's body under x-ray fluoroscopy, and a coating of a biocompatible material on said exposed metallic surface, said biocompatible material coating having a characteristic of shielding the patient's body tissue and blood from secondary radiation enhancement resulting from backscatter of x-ray radiation incident on said exposed metallic surface of the catheter body, wherein the biocompatible material for the coating is electrically conductive and has an atomic number which is considerably closer to the atomic number of body tissue than is the atomic number of the metallic surface.

18. The catheter of claim 17, wherein the biocompatible material for the coating comprises carbon material.

19. The catheter of claim 18, wherein the carbon material coating has a thickness in a range from about 50 $\mu$m to about 150 $\mu$m.

20. The catheter of claim 19, wherein said exposed metallic surface comprises a noble metal, and the carbon material coating has a thickness not exceeding about 100 $\mu$m.

21. A device for performing diagnostic or therapeutic functions in a human body, comprising an electrically non-conductive body portion, a metal portion of high fluoroscopic visibility overlying and in direct contact with said non-conductive body portion, and a substance of relatively low fluoroscopic visibility adherently overlying and in direct contact only with a major surface of said metal portion which is not in direct contact with said non-conductive body portion, said substance being electrically conductive and characterized by a property of substantially dissipating backscatter radiation, to inhibit backscatter of fluoroscopic radiation incident on said major surface of said metal portion.

\* \* \* \* \*